United States Patent [19]
Goldreyer

[11] Patent Number: 5,385,146
[45] Date of Patent: Jan. 31, 1995

[54] ORTHOGONAL SENSING FOR USE IN CLINICAL ELECTROPHYSIOLOGY

[76] Inventor: Bruce N. Goldreyer, 30311 Palos Verdes Dr. East, Rancho Palos Verdes, Calif. 90274

[21] Appl. No.: 1,980

[22] Filed: Jan. 8, 1993

[51] Int. Cl.[6] .................................................. A61B 5/04
[52] U.S. Cl. ................................. 128/642; 607/122; 607/154; 606/33
[58] Field of Search ................ 128/639, 642, 783–784, 128/785–786; 607/115, 116, 119, 122–124, 154; 606/13, 33, 27–31

[56] References Cited

U.S. PATENT DOCUMENTS

| | | | |
|---|---|---|---|
| 3,903,897 | 9/1975 | Woollons et al. | 128/642 X |
| 4,444,195 | 8/1984 | Gold | 128/642 |
| 4,649,924 | 3/1987 | Taccardi | 128/642 |
| 4,660,571 | 4/1987 | Hess et al. | |
| 4,699,147 | 10/1987 | Chilson et al. | 128/642 |
| 4,945,912 | 8/1990 | Langberg | 128/642 |
| 5,154,387 | 10/1992 | Trailer | 128/642 X |
| 5,179,952 | 1/1993 | Buinevicius et al. | 128/642 |

FOREIGN PATENT DOCUMENTS 1192263  8/1985  Canada .

OTHER PUBLICATIONS

Jackman et al. Circulation, Part 1, vol. 78, No. 3, Sep. 1988, "New Catheter Technique for Recording Left Free-Wall Accessory Atrioventricular Pathway . . . ".

Primary Examiner—Angela D. Sykes
Attorney, Agent, or Firm—Daniel L. Dawes

[57] ABSTRACT

Accurate mapping of electrophysiologic activation within the human heart is achieved for discrete areas within the heart by utilizing a catheter having at least one pair of orthogonal sensors disposed on the catheter. Orthogonal sensors, which are comprised of two or more electrodes generally disposed circumferentially on the catheter at given longitudinal position along the catheter, receive signals which are differenced within a differential amplifier to produce a signal indicative only of the localized or near field biopotential heart activity. The orthogonal sensors are disposed adjacent to the stimulating tip of the catheter to allow sensing of the localized cardiac activity which is adjacent to or in contact with the stimulating tip during pacing procedures or during the delivery of radio frequency energy during ablation. Sensing of the localized cardiac activity occurs simultaneously either with the pacing or the ablation so that detailed and accurate electrocardiograms of the stimulated or ablated tissue region can be recorded. A plurality of such a orthogonal sensors longitudinally disposed along the body of the catheter with spacings between each of them of 1-3 millimeters allows for simultaneous mapping of localized cardiac activation at a corresponding plurality of positions within the heart wall even when physical contact between the sensing electrodes and heart wall does not or cannot occur.

8 Claims, 1 Drawing Sheet

ORTHOGONAL SENSING FOR USE IN CLINICAL ELECTROPHYSIOLOGY

BACKGROUND OF THE INVENTION

1. Field of the Invention

The invention relates to the field of electrophysiology and more particularly to the sensing of intracardiac electrical patterns, a mapping of intracardiac electrophysiology, and the use of such sensing and mapping for clinical treatment.

2. Description of the Prior Art

The prior focus of electrophysiology has been directed to identifying the mechanisms of heart arrhythmias and evaluation of drug and other therapies upon the observed arrhythmias. Current studies in electrophysiology have continued to evolve to identify localized areas of abnormal myocardium as the sources of arrhythmias and to selectively remove or otherwise deactivate the abnormal myocardium. Obliteration has generally been practiced through localized ablation, generally using a short range radio frequency diathermy technique, although other energy sources such as laser energy, ultrasound and/or cyroprecipitation may also be used.

The treatment of heart arrhythmias has thus become increasingly dependent upon the ability to identify the precise location or origin in the myocardium of the abnormal rhythms. The prior art practice for locating the abnormal myocardium is to dispose a catheter within the heart chamber carrying a standard array of ring and tip electrodes. Direct contact of the tip electrode is used for making an intracardiac electrogram in a manner similar to that which has been practiced for many years with respect to pacemaker sensing. See, Imran, "Endocardial Mapping and Ablation System and Catheter Probe", U.S. Pat. No. 5,156,151 (1992).

One of the problems in prior art pacemaking has been the ability to simultaneously monitor the activity within the heart chamber while a large ventricular stimulating pulse was delivered through the catheter tip. One prior art solution is shown in Goldreyer, U.S. Pat. No. 4,365,639, wherein orthogonal sensing electrodes positioned on the catheter in the atrium were able to sense heart activity without being overwhelmed or saturated by the large ventricular stimulating pulse delivered through the catheter tip. In other words, because of the orthogonal placement of the sensing electrodes within the catheter body relative to the stimulating tip and the differential signal processing from the orthogonal electrodes, signals in the heart from directions other than the tip of the catheter could be preferentially sensed shortly after the large pacing and responsive ventricular pulse without saturation of the sensing circuitry.

What is needed is a method and apparatus for reliably mapping discrete electrophysiologic activity in the heart without the need to contact the heart walls and which can be done simultaneously with pacing or ablation procedures.

BRIEF SUMMARY OF THE INVENTION

The invention is a method for mapping electrophysiologic activation in a heart. The method comprises the steps of disposing a catheter within the heart at a predetermined position. Only localized cardiac signals from myocardium immediately adjacent to the predetermined position are sensed. The steps of disposing and sensing only the localized cardiac signals from a plurality of different predetermined positions within the heart are repeated. By this means accurate and discrete mapping of electrophysiologic activation within the heart is achieved.

The step of sensing only the localized cardiac signals from adjacent myocardium comprises the step of sensing the cardiac signals on at least a pair orthogonal electrodes disposed on the catheter at a position on the catheter near the predetermined position in the heart. The step of sensing is conducted without contacting the adjacent myocardium.

The step of sensing the cardiac signals on the orthogonal electrodes comprises the step of differencing cardiac signals received on each of the orthogonal electrodes to generate a differential signal therebetween. The differential signal is indicative of the localized cardiac activity.

The method further comprises the step of stimulating the adjacent myocardium while simultaneously sensing only localized cardiac signals from the adjacent myocardium. The step of stimulating is performed through a stimulating tip provided at a distal end of the catheter and a ring electrode 1–3 cm proximal from the tip and the step of simultaneously sensing is performed at position on the catheter proximate to the stimulating tip by means of at least a pair of orthogonal sensing electrodes. In the illustrated embodiment the step of sensing is performed at the position of the orthogonal electrodes approximately 1 to 5 millimeters spaced from the stimulating tip.

In another embodiment the step of sensing is performed at a plurality of positions on the catheter longitudinally disposed along the length of the catheter. In this case, the step of sensing along the plurality of positions longitudinally disposed on the catheter is performed at a corresponding plurality of orthogonal electrodes. The cardiac signal received by each of the plurality of orthogonal electrodes is differenced to produce a corresponding plurality of differential signals indicative of localized signals at each of the corresponding positions along the catheter.

The method further comprises the step of applying energy through the catheter at a predetermined position on the catheter for the purpose of ablation of myocardium at the predetermined position. The step of applying energy is performed by applying radio frequency ablative energy through an ablative tip at a distal end of the catheter. The step of sensing is simultaneously performed with the step of applying ablative energy.

The invention is also a catheter for mapping electrophysiologic activity within a heart which comprises a catheter body for disposition within the heart the catheter body having a distal tip. At least one pair of orthogonal electrodes is disposed on the catheter body at a predetermined position. A circuit is provided for receiving and differencing cardiac signals received by the at least one pair of orthogonal electrodes to generate a difference signal indicative of localized cardiac activity only at myocardium adjacent to the predetermined position of the orthogonal electrodes on the catheter. As a result, a catheter is provided for discretely and accurately mapping electrophysiologic activity within the heart.

The catheter further comprising a catheter tip disposed on the distal tip of the catheter. The catheter tip is arranged and adapted for delivery of a stimulating pulse for pacing the heart while simultaneously sensing the localized cardiac activity through the orthogonal electrodes. The orthogonal electrodes are disposed adjacent to the stimulating tip for simultaneous sensing of electrophysiologic activity in response to a pacing stimulus. In the illustrated embodiment the orthogonal electrodes are disposed within 1 to 3 millimeters from the stimulating tip.

The catheter further comprises an ablative electrode disposed on the catheter which is arranged and adapted for applying energy through the ablative tip to extirpate myocardium in contact with the ablative tip. The orthogonal electrodes are disposed adjacent to the ablative tip for simultaneously sensing electrophysiologic activation of myocardium subject to extirpation while ablative energy is applied to the myocardium.

The invention may be better visualized by now turning to the follow drawing wherein like elements are referenced by like numerals.

The invention and its various embodiments may now be better understood by turning to the following detailed description.

DETAILED DESCRIPTION OF THE PREFERRED EMBODIMENTS

Accurate mapping of electrophysiologic activation within the human heart is achieved for discrete areas within the heart by utilizing a catheter having at least one pair of orthogonal sensors disposed on the catheter. Orthogonal sensors, which are comprised of two or more electrodes generally disposed circumferentially on the catheter at given longitudinal position along the catheter, receive signals which are differenced within a differential amplifier to produce a signal indicative only of the localized or near field biopotential heart activity. The orthogonal sensors are disposed adjacent to the stimulating tip of the catheter to allow sensing of the localized cardiac activity which is adjacent to or in contact with the stimulating tip during pacing procedures or during the delivery of radio frequency energy during ablation. Sensing of the localized cardiac activity occurs simultaneously either with the pacing or the ablation so that detailed and accurate electrocardiograms of the stimulated or ablated tissue region can be recorded. A plurality of such orthogonal sensors longitudinally disposed along the body of the catheter with spacings between each of them of 1-3 millimeters allows for simultaneous mapping of localized cardiac activation at a corresponding plurality of positions within the heart wall even when physical contact between the sensing electrodes and heart wall does not or cannot occur.

Figure 1:
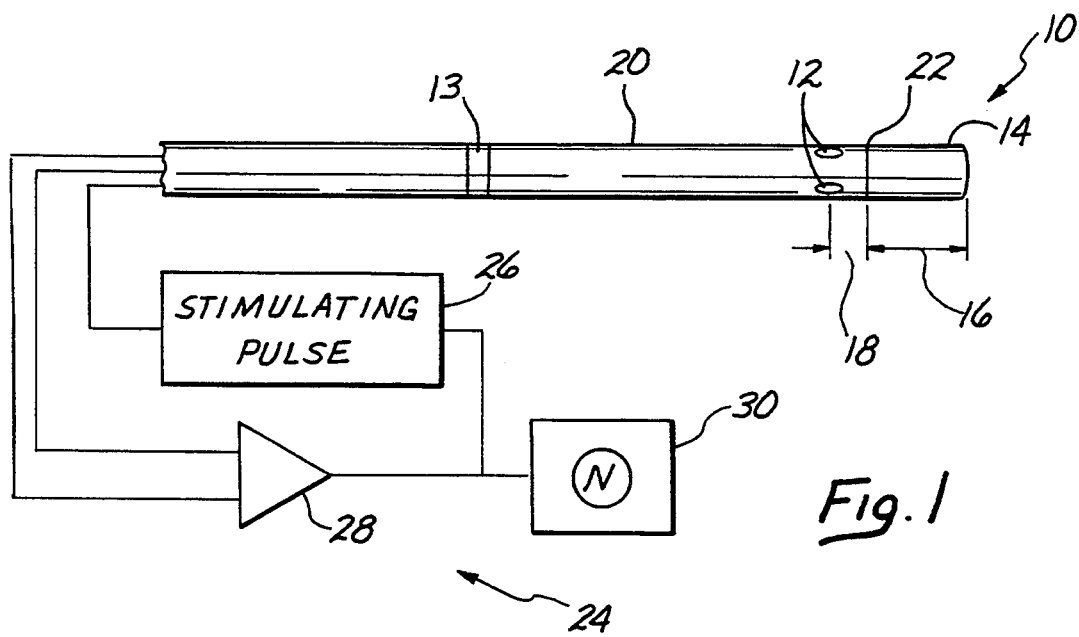
FIG. 1 is a diagrammatic depiction of a catheter employed according to the invention in which a single set of orthogonal electrodes are used.

FIG. 1 is a diagrammatic depiction of a catheter 10 incorporating a plurality of orthogonal sensing electrodes 12. Sensing electrodes 12 are disposed on catheter 10 behind a stimulating tip 14. In the embodiment of FIG. 1, tip 14 has a length 16 of approximately 2 to 4 millimeters. Any structure of stimulating tip 14 now known or later devised for ablation, pacing or other applications where energy or signals are transferred to myocardium may be used and are expressly contemplated as being within the scope of the invention.

Electrodes 12 are positioned in or on catheter body 20 at a distance 18 of approximately 1 to 3 millimeters behind or above the rearmost edge 22 of tip 14. Tip 14 and electrodes 12 are coupled to wires within catheter 10 and ultimately led to circuitry 24. The detail and nature of circuitry 24 is largely immaterial to the invention and therefore will not be further described other than to state that tip 14 is driven by a circuit 26 for generating a stimulating or ablating pulse and that sensing electrodes 12 are coupled in a pairwise fashion to one or more differential amplifiers 28 for generating a difference signal between selected ones of the electrodes. The difference signal is provided as an input to pulse generator 26 or to a monitor 30 to generate a time trace of the differential signal across two or more of the sensing electrodes 12. The difference signal may be subject to additional signal processing in conventional circuitry not explicitly depicted, such as signal conditioning or logical processing to develop the signal which is ultimately displayed in monitor 30 or used in pulse generator 26.

In the simplified embodiment of FIG. 1, only two orthogonal sensing electrodes 12 are shown although it is expressly contemplated that any number may be disposed within body 20 of catheter 10. For example, three such electrodes 12 may be disposed equal distantly around the circumference of body 20 of catheter 10 to provide from two to three differential signals for cardiac mapping.

It is also contemplated that monitor 30 may include a computer which will further process multiple signals from the plurality of differential amplifiers to generate various averages of the differential signals or other conventional statistical measures which will be indicative of the local electrical signals from the myocardial tissue proximate to sensing electrodes 12.

Still further, although sensing electrodes 12 have been shown in FIG. 1 to be disposed within a single circumferential, cylindrical band in body 20, it is also expressly contemplated that the electrodes may be displaced in a staggered fashion, that is one electrode placed further from edge 22 than another in order to provide both a different electrode pattern in space, but also to provide greater physical space on electrode 20 for the disposition of larger sensing electrodes. A ring electrode 13 may also be provided and used as part of a bipolar pacing array.

In this respect, whether electrodes 12 are insulated from contact with the blood, are provided with articulated surfaces for increasing the surface area available for blood contact without increasing the overall geometry of the sensing electrode, or otherwise incorporate various electrical improvements for coupling to circuitry 24 or for electrophysiological coupling is secondary to the invention which contemplates using any type orthogonal sensors now known or later devised, which are closely enough positioned with respect to stimulating tip 14 to provide an orthogonal electrogram of the myocardial activity in the proximity of tip 14. This is clearly advantageous where catheter 10 is used for local extirpation or ablation. A reliable identification of the abnormal myocardial site must be made in the proximity of the device which is used to obliterate or otherwise remove the abnormal tissue. In this sense, it is expressly contemplated that stimulating tip 14 may be replaced by any number of other different types of devices for extirpation or ablation to effect the removal or obliteration of the abnormal myocardium.

Figure 2:
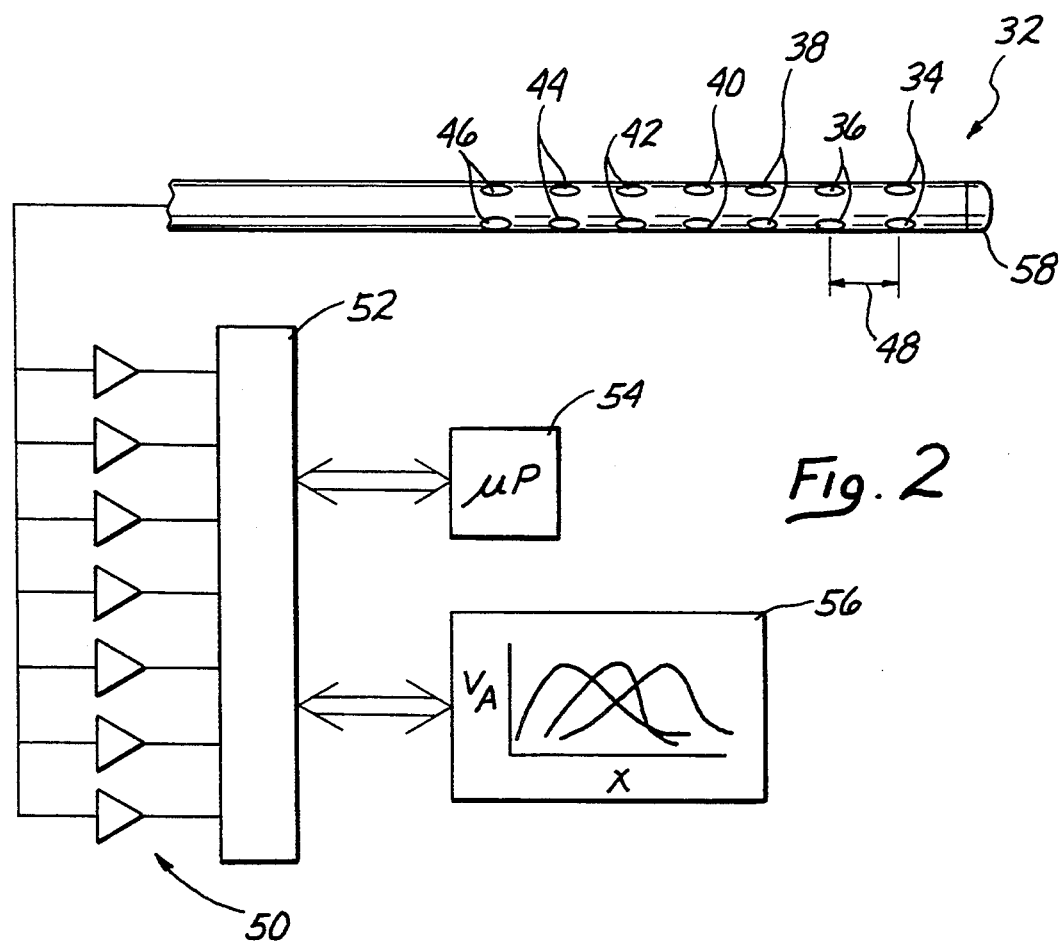
FIG. 2 is a diagrammatic depiction of a catheter employed according to the invention in which multiple sets of orthogonal electrodes are used.

FIG. 2 is a simplified depiction of another embodiment of the invention wherein a sensing catheter 32 is employed with a plurality of sets of orthogonal electrodes 34–46. In the illustrated embodiment of FIG. 2, each set is illustrated as being comprised of at least two electrodes and seven such sets are shown along the longitudinal length of catheter 32, although both the number of electrodes within each set as well as the number of sets on catheter 32 can be varied according to the application. Each set of electrodes 34–46 is separated from the adjacent set of electrodes 34–46 by a distance 48 of approximately 3 to 5 millimeters. Catheter 32 is a stearable cardiac catheter which can be used for activation mapping within the heart. Catheter 32 is laid against the atrial or ventricle walls or at least in the near proximity to them to monitor the direction of electrical activation. Direct contact with the myocardial tissue is not necessary. Signals from sets of electrodes 34–46 may be each individually coupled to the separate wire or multiplexed on a bus for input to a corresponding plurality of differential amplifiers 50. The output of amplifiers 50 are then provided after appropriate signal conditioning to digital bus 52 and computer 54 to provide an oscillographic or graphic map of the activation voltage by conventional output device 56, such as an oscilloscope or plotter. Again, the electronics which may be used in combination with the catheter of the embodiment of FIG. 2 is largely inconsequential and is suggested here only for the sake of completeness.

It has been determined that by use of a catheter having four pairs of orthogonal electrodes spaced at 5 millimeters apart in a configuration similar to that shown in FIG. 2 that differences of 16 milliseconds in the right atrium of the human heart can be easily recorded between sets of sensing orthogonal electrodes located only two centimeters apart and positioned along the lateral atrial wall. Therefore, a catheter of the type illustrated has particular utility for use in clinical electrophysiology for localizing a site within the heart from which abnormal rhythms originate. Catheter 32 is used to map the heart and to identify the area within the heart in which the surface activation in the heart most nearly identically matches that of a spontaneous arrhythmia either of a predetermined type or of a type actually measured from the patient from normal skin contact EKG. Such mapping and matching in three dimensions to a model of a patient's heart can be automated through computer 54 as contemplated in the context of the embodiment of FIG. 2.

Catheter 32 may also be provided with a stimulating tip 58 so that the heart can be stimulated during the mapping process to test heart functions or arrhythmias while the activation sequence of the near field heart potential is simultaneously sensed by each of the plurality of sets of orthogonal electrodes 34–46. Simultaneous sensing while pacing or stimulating cannot be performed with conventional ring electrodes which have a substantial signal pickup from the stimulating pulse. Simultaneous recording of localized electrograms can be accomplished in the present invention with either the single set of orthogonal electrodes 12 shown in FIG. 1 or with an array of such sets as shown in the embodiment of FIG. 2.

Recent investigations have revealed that intracardiac sensing according to the invention is so discrete that stimulation during the relative refractory period of the tissue will still detect a localized near potential of the tissue which is generated even prior to activation as seen on a surface EKG. As the stimulus is applied at earlier times during the period of tissue refractoriness, the orthogonal electrogram sensed by probes of the invention shows a cardiac response which becomes more and more fragmented with a delayed showing of the slow speed of excitation in the localized muscle. Therefore, the use of the sensing probes of the invention in pace mapping to find the sites within the heart of abnormal heart rhythms is particularly advantageous since reliable identification of such abnormal cites is based on upon being able to identify those areas of slow excitation responsible for reentry. Using orthogonal electrodes immediately behind a stimulating tip, the identified areas of slow excitation can be easily discriminated from areas of normal activation. This identification can then be exploited in subsequent steps of local extirpation or ablation.

The use of radio frequency localized diathermy for purposes of cardiac ablation is increasingly being used on abnormal heart muscle responsible for abnormal heart rhythms. Conventional catheter designs cannot record the myocardial activity of the ablated area during the ablation period. With orthogonal electrodes spaced at 1–3 mm proximal to the ablating tip according to the invention, energy can be applied to and cardiac recordings made of the local myocardial tissue as it is being subject to ablation. This allows direct observations to be made of localized signals and allows the physician to judge the efficiency of the ablation procedure in destroying the abnormal tissue.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the germ of the invention.

I claim:

1. A method for mapping electrophysiologic activation in a heart notwithstanding the presence of high intensity swamping signals for other purposes comprising the steps of:

disposing a catheter within said heart at a predetermined position;

sensing only localized cardiac signals from myocardium within 1 to 3 millimeters from said predetermined position by sensing said cardiac signals on at least a pair orthogonal electrodes disposed on said catheter within 1 to 3 millimeters of a position on said catheter near said predetermined position in said heart while said swamping signals are introduced into said heart; and repeating said steps of disposing and sensing only said localized cardiac signals from a plurality of different predetermined positions within said heart while said swamping signals are introduced into said heart, so that accurate and discrete mapping of electrophysiologic activation within said heart is achieved, wherein said step of sensing said cardiac signals on said orthogonal electrodes comprises the step of differencing cardiac signals received on each of said orthogonal electrodes to generate a differential signal therebetween, said differential signal being indicative of said localized cardiac activity.

2. A method for mapping electrophysiologic activation in a heart notwithstanding introduction of high intensity swamping signals for other purposes comprising the steps of:

disposing a catheter within said heart;

sensing only localized cardiac signals from myocardium within 1 to 3 millimeters from each of a plurality of positions on said catheter by a corresponding plurality of pairs of orthogonal sensing electrodes longitudinally disposed along the length of said catheter at said plurality of positions while said swamping signals are introduced into said heart; and repeating said steps of disposing and sensing only said localized cardiac signals from a plurality of different predetermined positions within said heart, so that accurate and discrete mapping of electrophysiologic activation within said heart is achieved even though said swamping signals are being simultaneously introduced into said heart, wherein said step of sensing along said plurality of positions longitudinally disposed on said catheter is performed at a corresponding plurality of orthogonal electrodes, said cardiac signal received by each of said plurality of orthogonal electrodes being differenced to produce a corresponding plurality of differential signals indicative of localized signals at each of said corresponding positions along said catheter.

3. A catheter for mapping electrophysiologic activity within a heart notwithstanding the presence of high intensity swamping signals for other purposes comprising:

a catheter body for disposition within said heart, said catheter body having a distal tip;

at least one pair of orthogonal electrodes disposed on said catheter body at a predetermined position;

means for receiving and differencing cardiac signals received by said at least one pair of orthogonal electrodes to generate a difference signal indicative of localized cardiac activity only at myocardium within 1 to 3 millimeters of said predetermined position of said orthogonal electrodes on said catheter; and a catheter tip electrode disposed on said distal tip of said catheter for introducing said swamping signal into said heart, said catheter tip electrode arranged and adapted for delivery of a stimulating pulse to a selected position in said myocardium for pacing said heart while simultaneously sensing said localized cardiac activity through said orthogonal electrodes at said predetermined position within 1 to 3 millimeters of said myocardium being stimulated for pacing at said selected position, whereby a catheter is provided for discretely and accurately mapping electrophysiologic activity within said heart.

4. The catheter of claim 3 wherein said orthogonal electrodes are disposed adjacent to said stimulating catheter tip electrode and simultaneously sense electrophysiologic activity in response to a pacing stimulus.

5. A catheter for mapping electrophysiologic activity within a heart notwithstanding the presence of high intensity swamping signals for other purposes comprising:

a catheter body for disposition within said heart, said catheter body having a distal tip;

at least one pair of orthogonal electrodes disposed on said catheter body at a predetermined position;

means for receiving and differencing cardiac signals received by said at least one pair of orthogonal electrodes to generate a difference signal indicative of localized cardiac activity only at myocardium within 1 to 3 millimeters of said predetermined position of said orthogonal electrodes on said catheter; and an ablative electrode disposed on said catheter for introducing said swamping signals into said heart by applying radio frequency energy through said ablative electrode to extirpate myocardium in contact with said ablative electrode, whereby a catheter is provided for discretely and accurately mapping and ablating electrophysiologic activity within said heart.

6. The catheter of claim 5 wherein said orthogonal electrodes are disposed within 1 to 3 millimeters of said ablative electrode for simultaneously sensing electrophysiologic activation of myocardium subject to extirpation while ablative energy is being applied to said myocardium.

7. A catheter for pacing a heart comprising:

a catheter body for disposition within said heart;

at least one pair of orthogonal electrodes disposed on said catheter body at a predetermined position for sensing localized cardiac activity only from myocardium within 1 to 3 millimeters of said predetermined position; and means for receiving and differencing cardiac signals received by said at least one pair of orthogonal electrodes to generate a difference signal indicative of localized cardiac activity only at myocardium within 1 to 3 millimeters of said predetermined position of said orthogonal electrodes on said catheter body, said means for receiving and differencing cardiac signals coupled to said at least one pair of orthogonal electrodes;

a catheter tip electrode disposed on said distal tip of said catheter, said catheter tip electrode being arranged and adapted for delivery of a stimulating pulse for pacing said heart; and wherein said orthogonal electrodes and means for receiving and differencing cardiac signals are arranged and adapted for simultaneously sensing said localized cardiac activity during delivery of said stimulating pulse to said catheter tip electrode, whereby said catheter is provided for stimulating said heart in response to localized cardiac signals from myocardium immediately adjacent to said orthogonal electrodes.

8. A catheter for ablation in a heart comprising:

a catheter body for disposition within said heart;

at least one pair of orthogonal electrodes disposed on said catheter body at a predetermined position for sensing localized cardiac activity only from myocardium within 1 to 3 millimeters of said predetermined position;

means for receiving and differencing cardiac signals received by said at least one pair of orthogonal electrodes to generate a difference signal indicative of localized cardiac activity only at myocardium within 1 to 3 millimeters of said predetermined position of said orthogonal electrodes on said catheter body, said means for receiving and differencing cardiac signals coupled to said at least one pair of orthogonal electrodes; and an ablative electrode disposed on said catheter arranged and adapted for applying energy through said ablative electrode to extirpate myocardium in contact with said ablative electrode; and wherein said orthogonal electrodes are disposed adjacent to said ablative electrode, said orthogonal electrodes and means for receiving and differencing cardiac signals being arranged and adapted for simultaneously sensing said localized cardiac activity of myocardium subject to extirpation while ablative energy is being applied to said myocardium through said ablative electrode, where by said catheter is provided for ablating selected myocardium in said heart in response to localized cardiac signals from myocardium immediately adjacent to said ablative electrode.

* * * * *